(12) United States Patent
Gupta et al.

(10) Patent No.: US 7,897,162 B2
(45) Date of Patent: Mar. 1, 2011

(54) ARTHROPOD REPELLENT PHARMACOPHORE MODELS, COMPOUNDS IDENTIFIED AS FITTING THE PHARMACOPHORE MODELS, AND METHODS OF MAKING AND USING THEREOF

(75) Inventors: Raj K. Gupta, Walkersville, MD (US); Apurba K. Bhattacharjee, Silver Spring, MD (US); Donna Ma Lee, Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 26 days.

(21) Appl. No.: 12/343,562

(22) Filed: Dec. 24, 2008

(65) Prior Publication Data

US 2009/0196838 A1  Aug. 6, 2009

Related U.S. Application Data

(62) Division of application No. 10/701,565, filed on Nov. 6, 2003, now Pat. No. 7,498,331.

(51) Int. Cl.
*A01N 25/08* (2006.01)
(52) U.S. Cl. ............... 424/411; 424/47; 424/59; 424/403; 424/412; 424/413; 424/414; 424/415; 424/416; 514/622; 514/678; 514/919
(58) Field of Classification Search ............ None
See application file for complete search history.

(56) References Cited

U.S. PATENT DOCUMENTS

| | | | |
|---|---|---|---|
| 4,127,672 A | 11/1978 | Klier et al. | |
| 4,707,496 A * | 11/1987 | Simmons | 514/531 |
| 4,869,896 A | 9/1989 | Coulston | |
| 4,883,801 A | 11/1989 | Nathanson | |
| 4,946,861 A * | 8/1990 | Weith et al. | 514/436 |
| 5,658,913 A * | 8/1997 | Kim et al. | 514/252.1 |
| 6,219,622 B1 | 4/2001 | Schmidt | |
| 6,524,605 B1 | 2/2003 | Coats | |

FOREIGN PATENT DOCUMENTS

WO  WO 2005/026193 A2  3/2005

OTHER PUBLICATIONS

Gouck et al ; Repellency- J. Econ. Entomol. 50, 175-7 1957.*
Bhattacharjee et al A 3-Dimensional Pharmacophore Model-129—Am.J. Trop.Med.Hyg. 67, #2 Suppl. 174-5 2002.*

(Continued)

*Primary Examiner*—Neil Levy
(74) *Attorney, Agent, or Firm*—Elizabeth Arwine

(57) ABSTRACT

Disclosed herein is a pharmacophore model for arthropod repellent activity and methods of making and using thereof. The pharmacophore comprises two hydrophobic aliphatic functions, one aromatic function and one hydrogen bond acceptor function. The pharmacophore model was made using a test set of arthropod repellent compounds. Also disclosed are arthropod repellent compounds identified by screening databases with the pharmacophore model. Also disclosed are methods of repelling arthropods from a surface or area. Compositions and formulations comprising the compounds of the present invention as well as objects having the compounds of the present invention are disclosed.

5 Claims, 7 Drawing Sheets

OTHER PUBLICATIONS

HCAPLUS abstract # 50:3283f-i, 3284a GILMAN et al some substtituted—acids & amides J. of Amer. Chem Soc. 77,6644-6, 1955.*

Dhami, et al Canadian J. of Chemistry, 43(2) 1965—13C NMR studies.*

Supplementary European Search Report, 4 pages, received in corresponding EP 03 78 3203, mailed Dec. 11, 2009.

J. Green, et al., "Chemical Function Queries for 3D Database Search", Journal of Chemical Information and Computer Sciences, American Journal Society, Columbus, Ohio, US, vol. 34. No. 6, Jan. 1, 1994, p. 1297-1308.

Arnold WN. (1989) "Evidence of the Pale-Green Liqueur's Toxicity Eventyally Extinguished the Fin-de-Siecle Infatuation with Absinthe" Sci Am. 260:112-117.

Bhattacharjee et al. (200) "Molecular Similarity Analysis Between Insect Juvenile Hormone and N,N-diethyl-m-toluamide (DEET) Analogs May Aid Design of Novel Insect Repellents" J Mol. Recognit. 13:213-220.

Dethier VG, et al. (1960) "The Designation of Chemicals in Terms of the Responses They Elicit from Insects" J. Econ. Entomol. 53:134-136.

Ewing HE (1925) "Sulphur-Impregnated Clothing to Protect Against Chiggers" J. Econ. Entomol. 18:827-829.

Carson LR and Winnike, ME (1968) "Relationships Between Insect Repellency and Chemical and Physical Parameters—A Review" J. Med. Entomol. 5:339-352.

Gleiberman SE, et al. (1976) "Study of the Remote Results of the Use of Repella" Med. Parazitol. (Mosk). 45:65-69.

Gupta RK and Rutledge LC (1994) "Role of Repellents in Vector Control and Disease Prevention" Am. J. Trop. Med. Hyg. 50(Suppl):82-86.

Kennedy JS. (1947) "The Excitant and Repellent Effects on Mosquitos Sub-Lethal Contacts with DDT" Bull. Entomol. Res. 37:593-607.

Are insect repellents safe? *Lancet* (1988) 2:610-611.

Ma, D et al. (1999) "Predicting Mosquito Repellent Potency of N,N-Diethyl-m-Toluamide (DEET) Analogs From Molecular Electronic Properties" Am. J. Trop. Med. Hyg. 60(1):1-6.

McCabe ET, et al. (1954) "Insect Repellents III N, N-Diethylamides" J. Org. Chem. 9:493-498.

Philip MI, et al. (1945) "Tumeric and Vegetable Oils as Repellents Against Anopheline Mosquitoes" Indian Med. Gaz. 80:343-344.

Rutledge LC, et al. (1986) "Sustained-Release Formulations of the U.S. Army Insect Repellent" Army Science Conference Proceedings 3:343-357.

International Search Report for PCT/US03/35425, 2 pages.

* cited by examiner

ARTHROPOD REPELLENT PHARMACOPHORE MODELS, COMPOUNDS IDENTIFIED AS FITTING THE PHARMACOPHORE MODELS, AND METHODS OF MAKING AND USING THEREOF

This application is a divisional of U.S. patent application Ser. No. 10/701,565, filed 6 Nov. 2003 now U.S. Pat. No. 7,498,331, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to a pharmacophore for arthropod repelling activity. In particular, the present invention relates to a pharmacophore derived from compounds exhibiting arthropod repellent activities.

2. Description of the Related Art

Arthropods can expose one to disease vectors, inflict severe physiological stress, and their bites can be painfully distracting and lead to devastating secondary infections, entomophobia, dermatitis, and allergic reactions. Four of the most important parasitic diseases of humans are arthropod-borne. Of the 80 diseases important to military operations, more than two thirds are transmitted by arthropods. See Defense Intelligence Agency (1982) *Handbook of Diseases of Military Importance*. Washington, D.C.: Government Printing Office, 135. Such diseases include malaria, dengue fever, West Nile fever, sandfly fever, yellow fever, viral encephalitis, filariasis, Japanese encephalitis, rift valley fever, leishmaniasis, Bartonellosis, sleeping sickness, myliasis, plague, typhus, tick-borne relapsing fever, tularemia, rocky mountain spotted fever, Ehrlichiosis, scrub typhus, and the like.

Use of insect repellents is a vital countermeasure in reducing arthropod-related casualties. A repellent is a chemical that causes the insect to make oriented movement away from its source. See Dethier V G, et al. (1960) J. Econ. Entomol. 53:134-136. Repellents may be classified based on their site of application or their mode of action. The two important types of insect repellents are topical repellents and clothing repellents. Based on the mode of action, insect repellents can be further classified as vapor (or olfactory or spatial) repellents and contact (or gustatory) repellents. Repellents such as DEET, dimethyl phthalate, and ethyl hexanediol depend on their vapors to keep insects at a distance, but the contact repellents, such as Indalone, are slightly volatile so that the insect must touch the treated surface before being repelled. See Garson, L R and Winnike, M E (1968) J. Med. Entomol. 5:339-352; Kennedy, J S (1947) Bull. Entomol. Res. 37:593-607; and Kennedy, J S (1947) Bull. Entomol. Res. 37:593-607.

Throughout human history various repellents have been used. Turmeric (*Curcuma longa*, Family Zingiberaceae) in vegetable oil was used daily for protection against mosquitoes. See Philip, M I, et al. (1945) Indian Med. Gaz. 80:343-344. Anatto (*Bixa orellana*, Bixaceae) in vegetable or animal oil. See Mom, A M (1948) Rev. Argentina da Dermatosifilologia 32:303-306. Wormwood juice (*Artemisia absinthium*, Compositae) to repel gnats and fleas. See Arnold, W N (1989) Sci. Am. 260:112-117. Leaves and fruits of citron (*Citrus medica*, Rutaceae) to repel insects from stored clothing. See Rice, E L (1983) *Pest Control with Nature's Chemicals: Allelochemics and Pheromones in Gardening and Agriculture*. Norman, Okla.: University of Oklahoma Press. Sulfur was dusted on skin and clothing to repel chiggers. See Ewing, H E (1925) J. Econ. Entomol. 18:827-829. Application of a 1:10 solution of Epsom salts (hydrated calcium sulfate). See US Army Medical Field Service School (1933) *Essentials of Field Sanitation for the Medical Department, United States Army*. Carlisle Barracks, Penn: US Army Medical Field Service School. Pyrethrum (*Chrysanthemum cinerariaefolium*, Compositae) and citronella (*Cymbopogon nardus*, Gramineae). See Gupta, R K and Rutledge, L C (1994) Am. J. Trop. Med. Hyg. 50 (Suppl):82-86.

The first synthetic repellents to gain wide acceptance were dimethyl phthalate and dibutyl phthalate. By the end of World War II, dimethyl phthalate, ethyl hexanediol (also called Rutgers 612), and Indalone (butyl-3,3-dihydro-2,2-dimethyl-4-oxo-2H-pyran-6-carboxylate) had been identified as superior mosquito repellents. See Stage, H H (1952) Mosquitoes. In: Stefferud A, ed. *Insects: The Yearbook of Agriculture*. Washington, D.C.: US Government Printing Office, 476-486. Unfortunately, in 1991 the US Environmental Protection Agency (EPA) canceled all registrations of ethyl hexanediol at the request of its manufacturers because of new information on possible adverse fetal developmental effects. See US Environmental Protection Agency (1991) 2-ethyl-1,3-hexanediol; receipt of requests to cancel. Fed. Reg. 8:4376-43768.

Perhaps the single most important event in the evolution of repellents was the discovery of DEET in 1954. See McCabe, E T, et al. (1954) J. Org. Chem. 9:493-498. DEET has virtually eclipsed other repellents for topical use, and remains the principal repellent in use today, more than 40 years after its discovery. Even though DEET is an effective repellent against a broad spectrum of arthropods, it has several drawbacks. Under warm, humid conditions, the application lasts for only 1 to 2 hours. DEET is a strong plasticizer, has a disagreeable odor, and feels "oily". DEET has been associated with allergic and toxic effects in some people, especially when used repeatedly on the skin in high concentrations. A report in 1976 showed regular applications of DEET on the skin of white rats was gonadotoxic and embryotoxic. See Gleiberman, S E, et al. (1976) Med. Parazitol. (Mosk). 45:65-69. DEET has been associated with bullous eruptions in the antecubital fossa and contact urticaria, and rare cases of toxic encephalopathy have occurred with excessive or prolonged use, particularly in infants and children. See Are insect repellents safe? *Lancet* (1988) 2:610-611. Use of DEET has been implicated in seizures among children.

Unfortunately, progress in the development of new repellents has been limited. One important reason for the lack of success in this area is the limited understanding of the repellents' mode of action on the target organisms. The general assumption that all repellents affect all arthropods in the same way is incorrect. It has been shown that even strains of the same species differ significantly in their tolerance to the same repellent. Therefore, selection of appropriate repellents for personal protection greatly depends on the species to be repelled. Also, a certain minimum effective evaporation rate of repellent is required to effectively repel insects. See Rutledge, L C, et al. (1986) Army Science Conference Proceedings 3:343-357.

Thus, a need exists for more effective repellents having less side-effects and methods for screening candidate compounds for repellent activity.

SUMMARY OF THE INVENTION

The present invention generally relates to a pharmacophore model for arthropod repellent activity.

In some embodiments, the present invention relates to a pharmacophore for arthropod repellent activity of a compound comprising two hydrophobic aliphatic functions, one aromatic function and one hydrogen bond acceptor function.

In some embodiments, the pharmacophore of the present invention is made by (a) generating a set of three-dimensional conformers for each of the compounds in a training set comprising at least five compounds known to exhibit arthropod repellent activity, (b) correlating each of the compounds of the training set with at least one observed $IC_{50}$ value of the arthropod repellent activity, (c) generating from the set of three-dimensional conformers at least one hypothesis, (d) calculating the arthropod repellent activity for each conformer of step (a) towards the hypothesis, (e) calculating the total cost for the hypothesis, and (f) selecting the hypothesis with the lowest cost as the pharmacophore. In some preferred embodiments, at least one of the compounds known to exhibit the arthropod repellent activity is DEET. In some embodiments, the steps are carried out using a molecular modeling software program such as CATALYST®. In some embodiments, the observed $ED_{50}$ value of arthropod repellent activity ranges from about 1 µg/cm² to about 50 mg/cm², preferably about 1 µg/cm² to about 25 mg/cm², more preferably about 1 µg/cm² to about 10 mg/cm², most preferably about 1 µg/cm² to about 5 mg/cm². In some embodiments, the observed $ED_{50}$ value of arthropod repellent activity ranges about 3.0 µg/cm² to about 21 µg/cm². In some preferred embodiments, the energy range of the set of three-dimensional conformers is about 0 to about 25 Kcal/mole.

In some preferred embodiments, the pharmacophore of the present invention comprises the following X, Y, and Z coordinates of the two hydrophobic aliphatic functions, one aromatic function and one hydrogen bond acceptor function:

| Coordinates | HBA lipid | | Hydro-phobic | Hydro-phobic | Aromatic |
| --- | --- | --- | --- | --- | --- |
| | First Focal Point | Second Focal Point | | | |
| weights | 1.83893 | | 1.83893 | 1.83893 | 1.83893 |
| tolerances | 1.60 | 2.20 | 1.60 | 1.60 | 1.60 |
| X | 5.35 | 4.92 | 1.35 | −0.06 | 3.34 |
| Y | 2.88 | 5.82 | 0.72 | −0.70 | 2.81 |
| Z | 1.60 | 1.20 | −1.27 | 0.94 | −2.71 |

In some embodiments, the pharmacophore of the present invention comprises a root mean square equivalent functions of less than about 3.0 Å of the two hydrophobic aliphatic functions, one aromatic function and one hydrogen bond acceptor function of the following X, Y, and Z coordinates of the two hydrophobic aliphatic functions, one aromatic function and one hydrogen bond acceptor function:

| Coordinates | HBA lipid | | Hydro-phobic | Hydro-phobic | Aromatic |
| --- | --- | --- | --- | --- | --- |
| | First Focal Point | Second Focal Point | | | |
| weights | 1.83893 | | 1.83893 | 1.83893 | 1.83893 |
| tolerances | 1.60 | 2.20 | 1.60 | 1.60 | 1.60 |
| X | 5.35 | 4.92 | 1.35 | −0.06 | 3.34 |
| Y | 2.88 | 5.82 | 0.72 | −0.70 | 2.81 |
| Z | 1.60 | 1.20 | −1.27 | 0.94 | −2.71 |

In preferred embodiments, the root mean square is less than about 1.5 Å, preferably less than about 1.0 Å, more preferably, less than about 0.5 Å.

In some embodiments, the present invention provides a method for screening a candidate compound for arthropod repellent activity which comprises (a) finding the best fit of the candidate compound to the pharmacophore of the present invention, and (b) calculating the activity value for the candidate compound. In some preferred embodiments, the best fit is determined using a fast-fit algorithm, a principle component analysis, a partial least squares technique, a linear regression technique, or a non-linear regression technique.

In some embodiments, the present invention provides a compound having arthropod repellent activity identified by the method of screening candidate compounds according to the present invention. In some embodiments, the present invention provides a composition which comprises at least one compound having arthropod repellent activity identified according to the present invention. In some embodiments, the composition is a lotion, a cream, a foam, an aerosol, a face paint, a stick, a soap, or a sunscreen product.

In some embodiments, the present invention provides a method of repelling an arthropod from a surface of a substrate, an area, or a mammal which comprises administering to the surface, the area, or the mammal an effective amount of at least one compound of identified by the methods of the present invention. In some preferred embodiments, the compound is N,N-diethyl-2-(3-trifluoromethyl-phenyl)-acetamide, 2-cyclohexyl-N,N-diethylacetamide, N,N-diethyl-2-(3-bromo-phenyl)-acetamide, N,N-diethyl-3-trifluoromethyl-benzamide, 2-bromo-1-(2,5-dimethoxy-phenyl)-ethanone, 2-methyl-1-(2,3,5,6-tetramethyl-phenyl)-propan-1-one, 2-allylsulfanyl-3-methyl-pyrazine, 2-(2-chloro-phenoxy)-2-methyl-propionamide, or 5-[5-(1-hydroxy-nonyl)-tetrahydro-furan-2-yl]-pentanoic acid.

In some embodiments, the substrate is a fabric, an article of clothing, a bed net, a curtain, a paper, a wall paper, a window screen, a ground cloth, a tent, a towelette, or a protective overgarment. In some embodiments, the compounds is formulated into a lotion, a lotion, a cream, a foam, an aerosol, a face paint, a stick, a soap, a sunscreen product, or a cosmetic.

In some embodiments, the present invention provides a substrate which comprises at least one compound having arthropod activity identified according to the present invention.

In some embodiments, the present invention provides kits comprising at least one compound having arthropod activity identified according to the present invention packaged together with instructions for use.

In some embodiments, the present invention provides a method of determining the arthropod repellent activity or potency of a candidate compound which comprises (a) generating three-dimensional descriptors for the candidate compound, (b) inputting the three-dimensional descriptors into an equation relating to the observed arthropod repellent activity of a set of arthropod repellent compounds to a set of three-dimensional descriptors for the set of arthropod repellent compounds, and (c) solving the equation for the arthropod repellent activity or potency of the candidate compound corresponding to the three-dimensional descriptors of step (a).

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
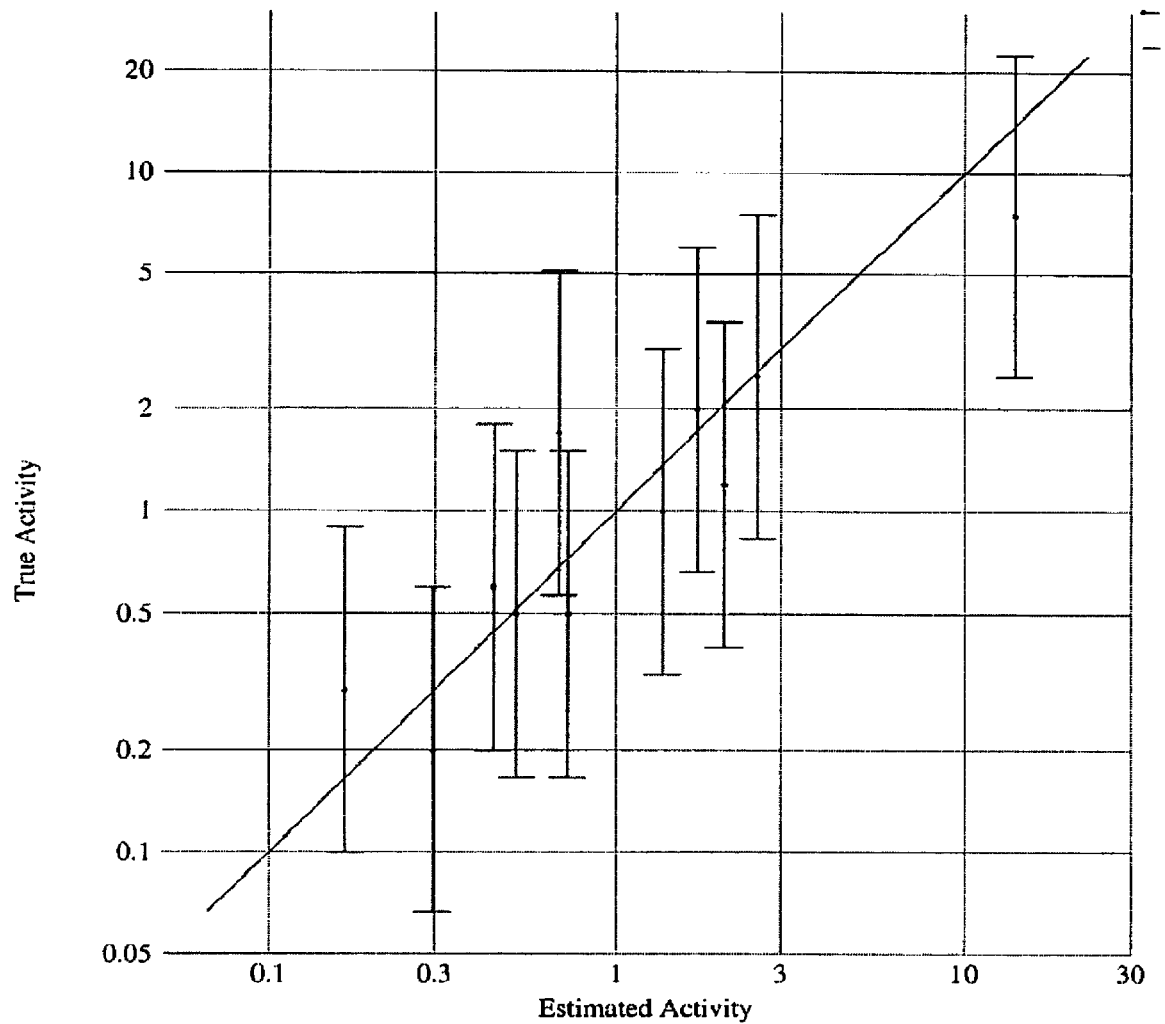
FIG. 1 shows the correlation between the protection (repelling) time conferred by the compounds in the training set and their predicted protection (repelling) time. Correlation Between Experimental PT and Estimated PT (R=0.91)

In order to better understand insect repellent properties of various compounds, a three-dimensional pharmacophore model using 3D-Catalyst from a training set of eleven diverse insect repellent compounds, including DEET, was generated. Protection time data for repellent activity of the training set were taken from an earlier published study. As disclosed herein, the pharmacophore model comprises three hydrophobic sites and a hydrogen-bond acceptor site. The calculated stereoelectronic properties such as molecular electrostatic potentials on DEET and some of the compounds in the training set were consistent with the three hydrophobic sites and a hydrogen-bond acceptor site. The pharmacophore exhibits a good correlation, about 0.91, between the protection (repelling) time conferred by the compounds in the training set and their predicted protection (repelling) time. See FIG. 1. As disclosed herein, the validity of the pharmacophore goes beyond that of the training set and was found to map well on a variety of other repellents.

Although CATALYST® 4.7 software (Accelrys Inc., San Diego, Calif.) was used for 3D QSAR analysis and pharmacophore generation, other methods known in the art such as those described in PHARMACOPHORE PERCEPTION, DEVELOPMENT, AND USE IN DRUG DESIGN (2000) Ed. Osman F. Gunner, International University Line, La Jolla, Calif., may be used according to the present invention.

As disclosed in Example 2, molecular modeling software, CATALYST® 4.7 software (Accelrys Inc., San Diego, Calif.) was used to construct a three-dimensional QSAR pharmacophore model for the repellent activities exhibited by some repellent compounds known in the art. A training set of 11 structurally diverse arthropod repellent compounds having a broad range of repellent activities shown in Table 1 were used to construct the pharmacophore model. Although more or less compounds in the training set may be used, in preferred embodiments, about 10 to about 20 chemically diverse molecules with biological activity covering 4 to 5 orders of magnitude for the training set are used.

TABLE 1

Training Set of 11 Different Repellents

| Compound | Experimental PT (hr) | Estimate PT (hr) | Error |
|---|---|---|---|
| DEET | 1.0 | 1.4 | 1.4 |
| N,N-diethyl-2-ethoxybenzamide | 0.5 | 0.73 | 1.5 |
| N,N-dipropyl-2-benzyloxyacetate | 0.5 | 0.52 | 1.0 |
| 1-butyl-4-methylcarbostyril | 2.0 | 1.7 | −1.2 |
| N,N-dipropyl-2-ethoxybenzamide | 0.3 | 0.17 | −1.8 |
| 2-butyl-2-ethyl-1,3-propanediol | 1.7 | 0.68 | −2.5 |

TABLE 1-continued

Training Set of 11 Different Repellents

| Compound | Experimental PT (hr) | Estimate PT (hr) | Error |
|---|---|---|---|
| 1,3-bisbutoxymethyl-2-imidazol | 0.6 | 0.44 | −1.4 |
| N,N-diethyl-2-chlorobenzamide | 1.2 | 2.1 | 1.7 |
| Hexachlorophenol | 0.2 | 0.3 | 1.5 |
| 1,3-propanediolmonobenzoate | 7.5 | 14.0 | 1.9 |
| Diisobutylmalate | 2.5 | 2.6 | 1.0 |

The repellent activity of the 11 repellent compounds in the training set covers a broad range of activity, from an $ED_{50}$ of about 1 µg/cm² to about 50 mg/cm².

The structures of the training set were either imported into or edited within CATALYST® by assembling the structural fragments and energy minimized to the closest local minimum using the CHARMM-like force field. Molecular flexibility was taken into account by considering each compound as an ensemble of conformers representing different accessible areas in a three dimensional space. The "best searching procedure" was applied to select representative conformers within about 20 kcal/mol above the calculated global minimum. See Grigorov, M, et al. (1995) J. Chem. Inf. Comput. Sci. 35:285-304, which is herein incorporated by reference.

Hypothesis generation was carried out with the training set of 11 repellent compounds by methods known in the art. See Greenridge, P A and J. Weiser (2001) Mini Reviews in Medicinal Chemistry 1:79-87; Grigorov, M, et al. (1995) J. Chem. Inf. Comput. Sci. 35:285-304; which are herein incorporated by reference. At an ASTMH 2002 meeting in Denver, Colo., information about the pharmacophore for arthropod repelling activity was presented. It should be noted, however, that the coordinates of the pharmacophore model were not disclosed at the meeting. Therefore, the information disclosed at the meeting did not constitute an enabling public disclosure.

Figure 2:
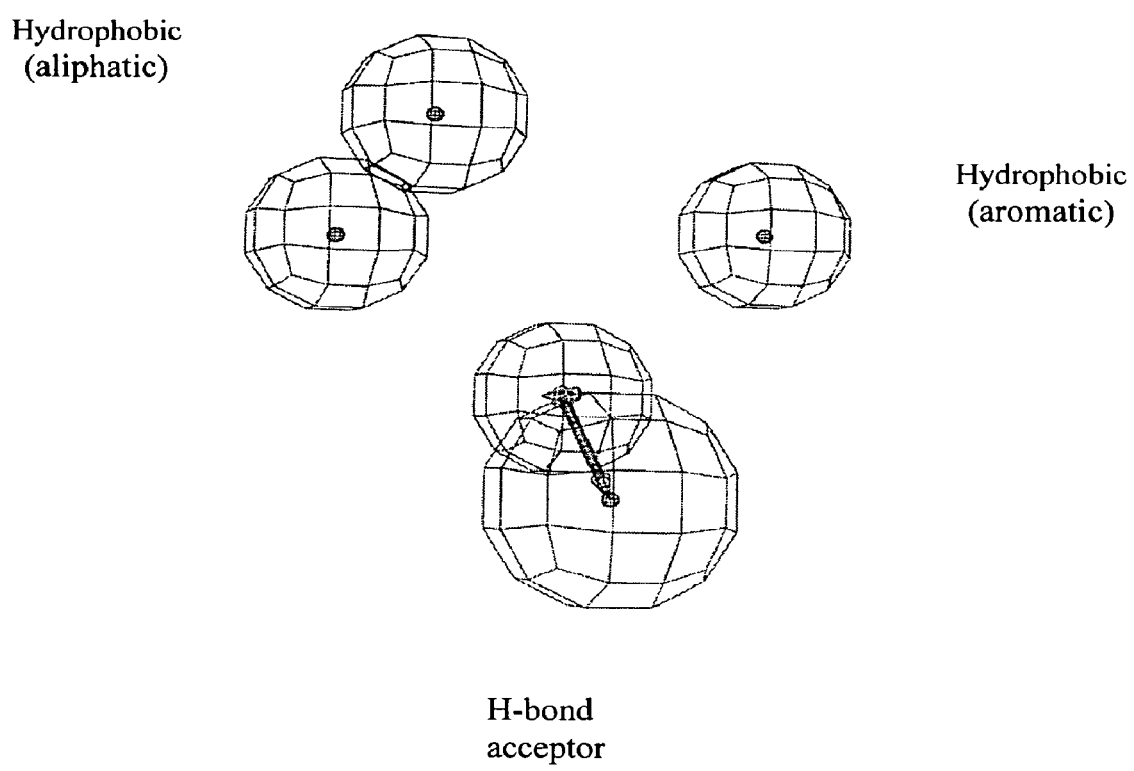
FIG. 2 represents the pharmacophore model of the present invention that is characterized by two hydrophobic aliphatic functions, one aromatic function and one hydrogen bond acceptor function.

FIG. 2 represents the statistically most relevant hypothesis which is characterized by two hydrophobic aliphatic functions, one aromatic function and one hydrogen bond acceptor function See Greene, et al. (1994) J. Chem. Inf. & Comp. Sci. 34:1297-1308, which is herein incorporated by reference. The hydrogen boding features are vectors, whereas all other functions are points. The statistical relevance of the obtained hypothesis was assessed on the basis of their cost relative to the null hypothesis and their correlation coefficient.

The coordinates of the pharmacophore model represented by FIG. 2 are set forth in angstroms in Table 2 and define the relative relationship between the features.

TABLE 2

| Coordinates | HBA lipid | | Hydrophobic | Hydrophobic | Aromatic |
|---|---|---|---|---|---|
| | First Focal Point | Second Focal Point | | | |
| weights | 1.83893 | | 1.83893 | 1.83893 | 1.83893 |
| tolerances | 1.60 | 2.20 | 1.60 | 1.60 | 1.60 |
| X | 5.35 | 4.92 | 1.35 | −0.06 | 3.34 |
| Y | 2.88 | 5.82 | 0.72 | −0.70 | 2.81 |
| Z | 1.60 | 1.20 | −1.27 | 0.94 | −2.71 |

The coordinates are dependent upon the particular coordinate system used, and those skilled in the art will recognize that, although rotation and translation of these coordinates may change the specific values of these coordinates, they will in fact define the pharmacophore model of the present invention. The pharmacophore model of the present invention is intended to encompass any model, after optimal superposition of the models, comprising the identified features and having a root mean square of equivalent features of less than about 3.0 Å. More preferably, the pharmacophore model of the present invention encompasses any model comprising the features identified herein and having a root mean square of equivalent features of less than about 1.5 Å, even more preferably, less than about 1.0 Å, and most preferably less than about 0.5 Å.

As those of skill in the art will readily recognize, chemically different substructures can present certain identical three-dimensional space-filling features, and accordingly, the models of the present invention comprise features that may or may not correspond to actual functional groups in any given repellent compound. Additionally, since compounds having different structural formulas may have the same or similar pharmacophore hypotheses, the compounds of the present invention are not limited to compounds having similar chemical structures.

CATALYST® software allows mapping of all functions generated in a pharmacophore to the more potent analogues and fewer or none in the less potent analogues of the training set through conformational energy and best-fit scoring calculations. The technique involves a 3D screening of all the conformations of the molecule by matching the pharmacophore features. See Kurogi, Y and Gunner, O F (2001) Current Medicinal Chemistry 8:1035-1055, which is herein incorporated by reference.

As provided in Example 3, the pharmacophore model may be cross-validated by using a test set of repellent compounds known in the art. The test set compounds may be screened for repellent activity by the assays provided in Example 1 or other methods known in the art and then compared with the repellent activity of those compounds in the original training set. The validity of the pharmacophore model to other commonly used repellent compounds may be examined. The pharmacophore features may be mapped onto the repellent compounds and should be found to map significantly well with known repellent compounds to varying degrees.

There are 3 parameters such as the "best-score fit", estimate of activity, and conformational energy costs are involved in the present case to assess the quality of the pharmacophore mapping. The mapping of a pharmacophore on the three-dimensional structure of a compound is carried out by means of a few calculations. The compound to be mapped to a pharmacophore is converted to a three-dimensional configuration and all its conformations with energies are stored in a computer which then performs the analytical calculations which compares the three-dimensional comformers of the compound being mapped and the pharmacophore. Perfect mapping means that the features of the pharmacophore matches exactly with at least one of the conformers of the compound. "Best-fit scores" indicate the degree of matching, conformational energy indicates how much of energy would be spent by the molecule to match the pharmacophore, and estimate of activity is the prediction of activity should the compound be a member of the training set from the pharmacophore was originally developed.

Figure 3:
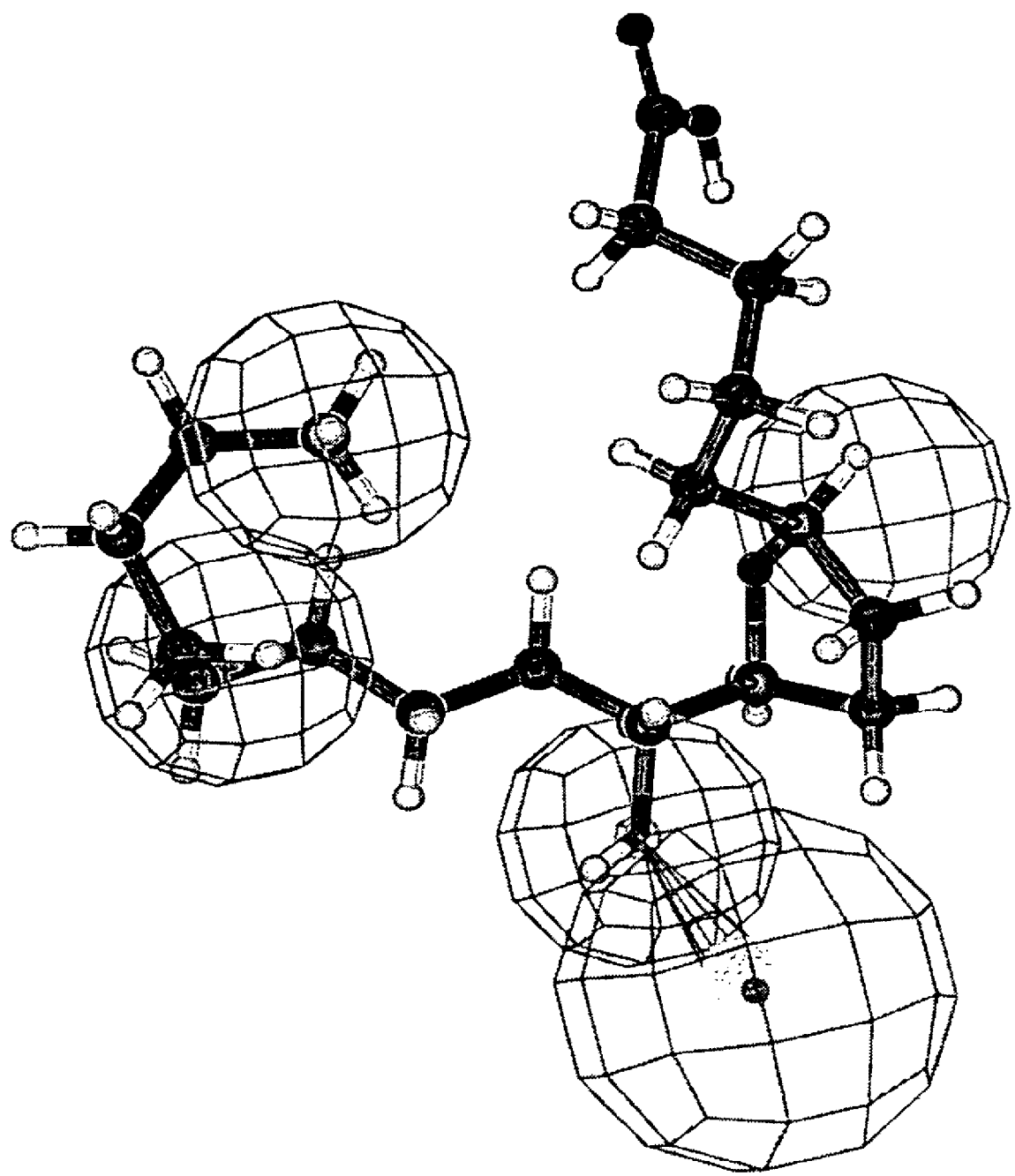
FIG. 3 shows the pharmacophore model of the present invention mapped onto 5-[5-(1-hydroxy-nonyl)-tetrahydro-furan-2-yl]-pentanoic acid.
Figure 4A:
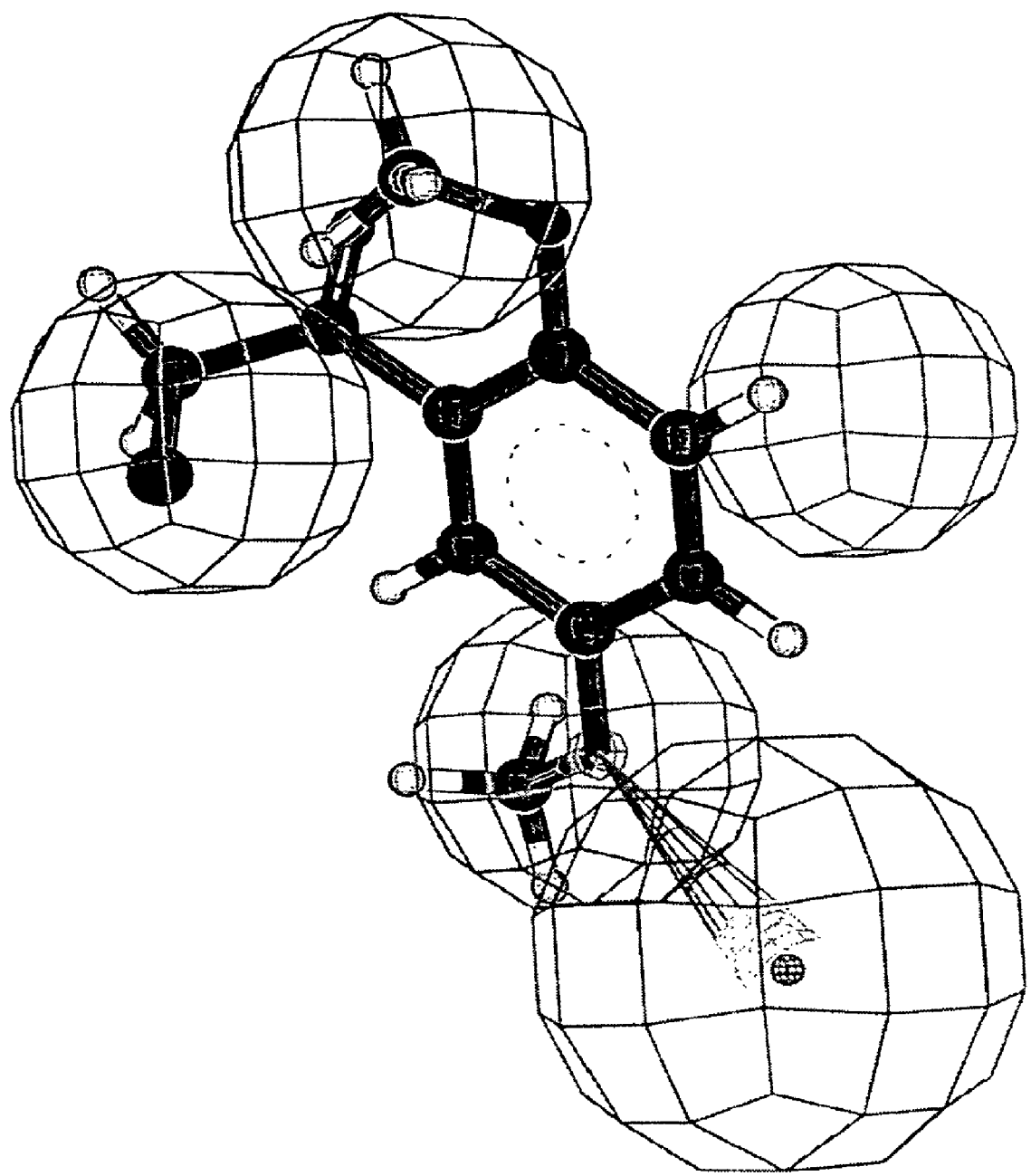
FIG. 4A shows the pharmacophore model of the present invention mapped onto 2-bromo-1-(2,5-dimethoxy-phenyl)-ethanone.
Figure 4B:
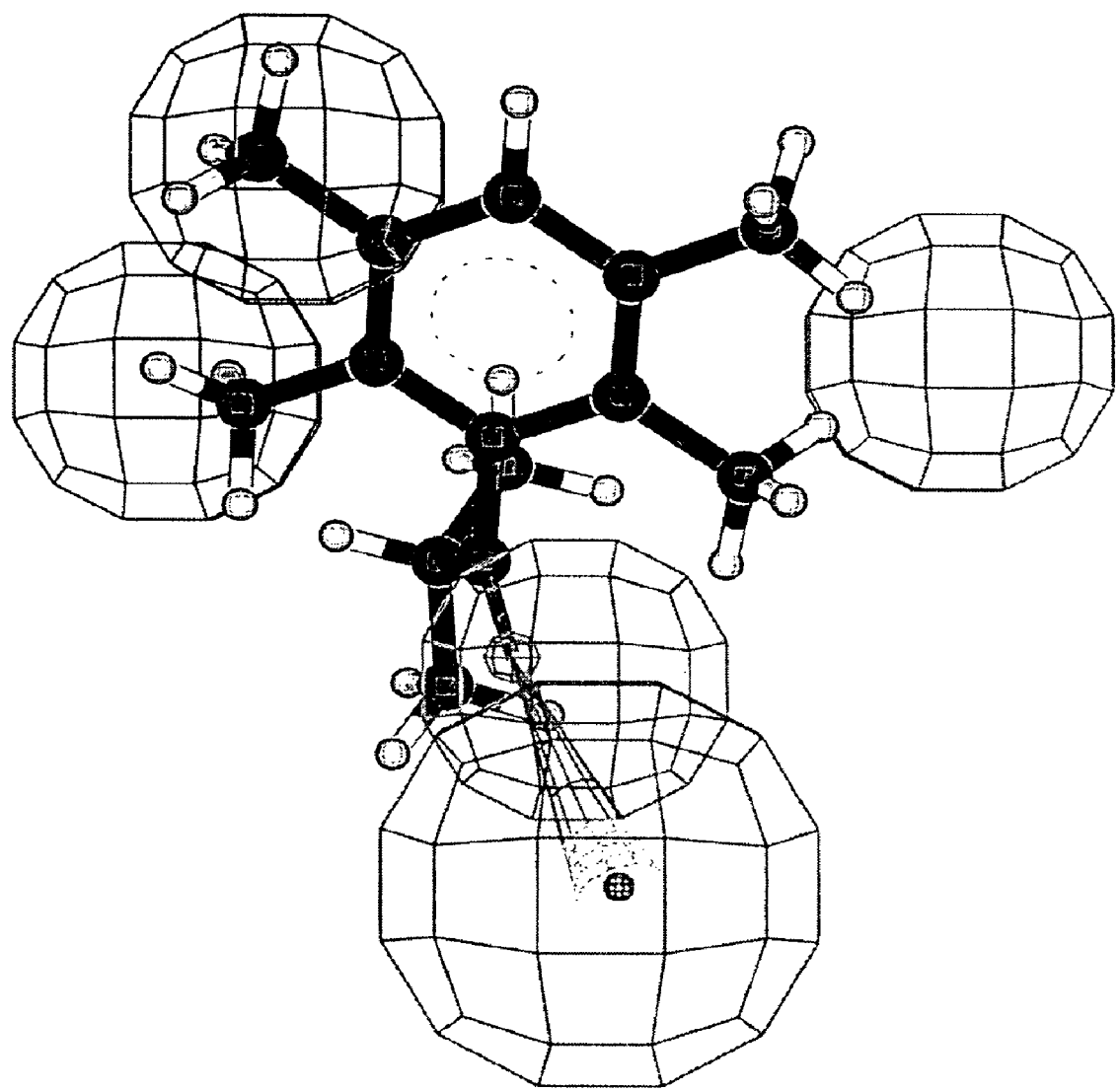
FIG. 4B shows the pharmacophore model of the present invention mapped onto 2-methyl-1-(2,3,5,6-tetramethyl-phenyl)-propan-1-one.
Figure 4C:
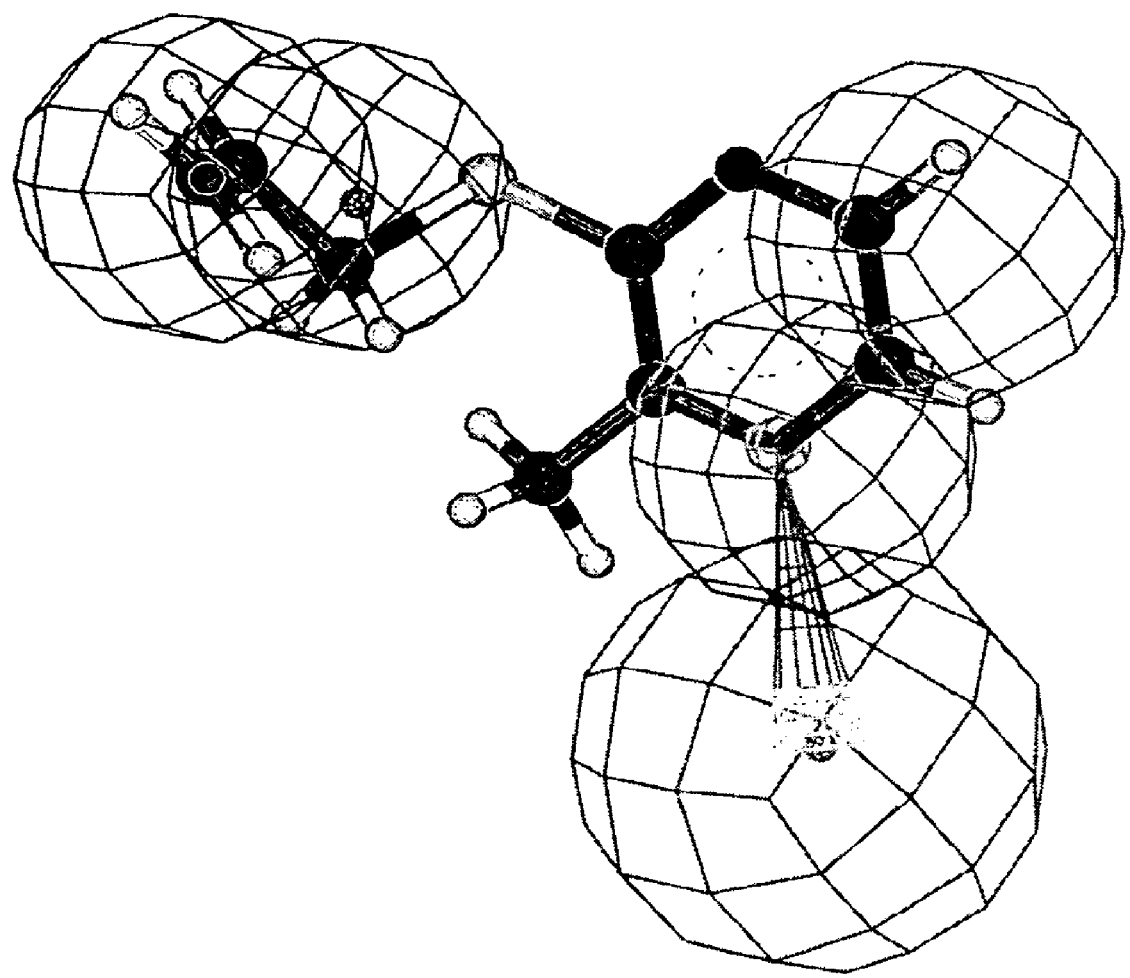
FIG. 4C shows the pharmacophore model of the present invention mapped onto 2-allylsufanyl-3-methyl-pyrazine.
Figure 4D:
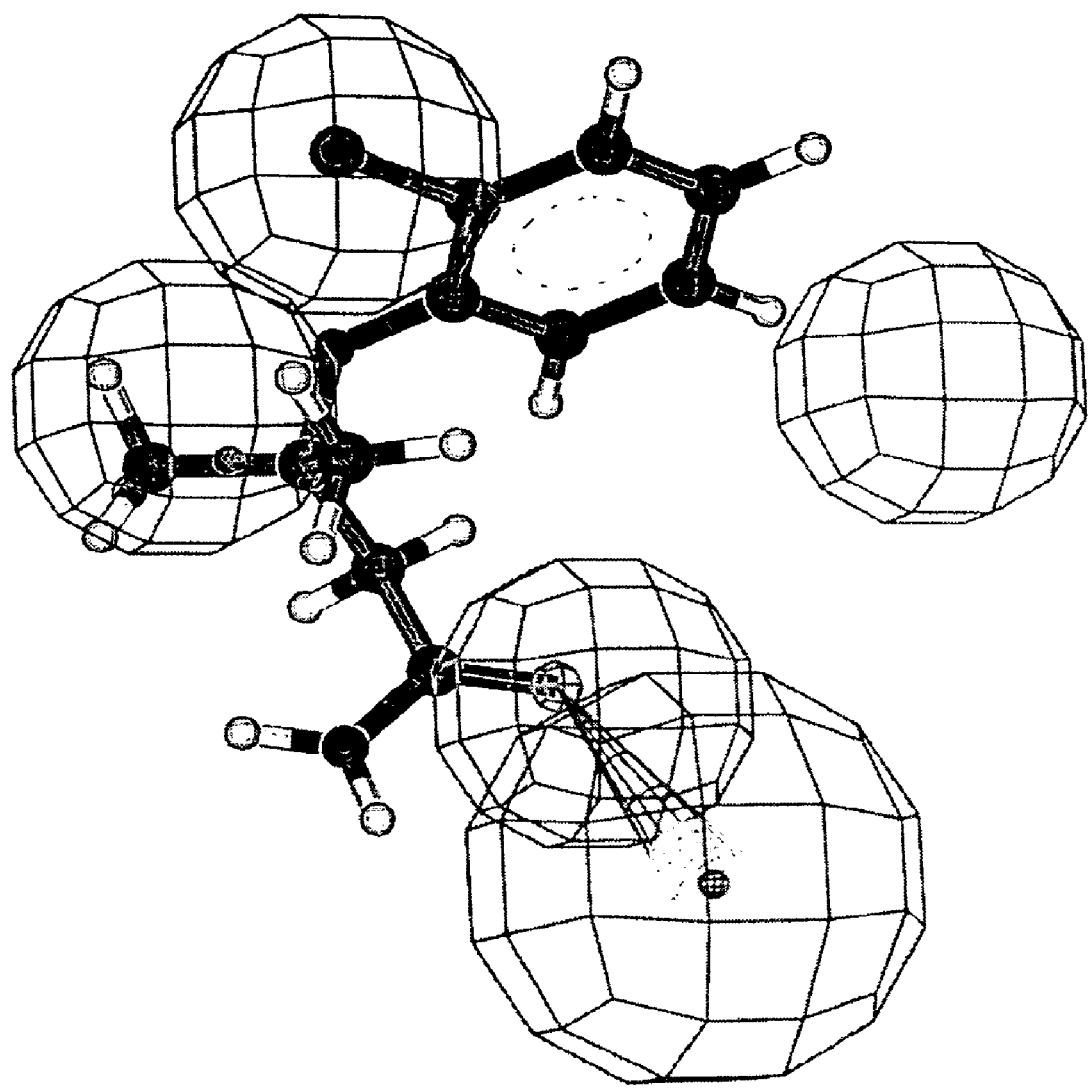
FIG. 4D shows the pharmacophore model of the present invention mapped onto 2-(2-chloro-phenoxy)-2-methyl-propionamide.

Recently, a novel 18-carbon acid was isolated from samples of greasy guar hair that acts as a landing and feeding deterrent for mosquitoes was discovered. See Oliver, J E and Patterson, K S (2003) C&EN, p. 49, which is herein incorporated by reference. The pharmacophore model of the present invention mapped significantly well to the compound, 5-[5-(1-hydroxy-nonyl)-tetrahydro-furan-2-yl]-pentanoic acid with a best fit score of about 5.4. See FIG. 3.

As provided in Example 4, the pharmacophore model of the present invention was used to search three-dimensional multiconformer databases, including an in-house Chemical Information System (Chemical Information System, Division of Experimental Therapeutics, Walter Reed Army Institute of Research, Silver Spring, Md.), National Cancer Institute, IBS and Maybridge databases, to screen for potential new repellent agents. The Chemical Information System database has over 240,000 compounds and was transformed into a multiconformer database in CATALYST® using the catDB® utility program as implemented in the software. The catDB® format allows a molecule to be represented by a limited set of conformations thereby permitting conformational flexibility to be included during the search of the database.

Specifically, the three-dimensional pharmacophore of the present invention was used as a template for search various three-dimensional multi-conformer databases. Three-dimensional multi-conformer databases of molecules comprise all possible conformations of the three-dimensional structure of each molecule in the database within an energy range of 0 to 25 kcal/mol. The three-dimensional structures in the databases were mapped to or compared with the three-dimensional pharmacophore of the present invention to identify compounds having the same or similar three-dimensional conformations.

The compounds were short listed on the basis of their ADME (Absorption, Distribution, Metabolism, and Excretion) properties and were evaluated by rapid in silico screening using Cerus$^2$ADME methodology. See Cerus$^2$ADME. Accelrys Inc. (2003) San Diego, Calif. The short listed compounds were then tested for arthropod repellent property using methods known in the art. See e.g. Debboun, et al. (1999) J. Am. Mosq. Cont. Assoc. 15(3):342-347; and Gupta, R K and Rutledge, L C (1991) J. Am. Mosq. Cont. Assoc. 7:490-493, which are herein incorporated by reference. Eight compounds were found to have excellent arthropod repellent activity as shown in Table 3. Experimental and predicted Protection Time (PT) of the eight these compounds are provided in Table 3 as follows:

TABLE 3

| Compound | Experimental PT (hr) | Estimate PT (hr) |
|---|---|---|
| N,N-diethyl-2-(3-trifluoromethyl-phenyl)-acetamide (DM156(D2)) | 0.14 ($ED_{50}$ = 3.0) | 0.12 |
| 2-cyclohexyl-N,N-diethylacetamide (DM 36-2) | 0.24 ($ED_{50}$ = 4.9) | 3.6 |

TABLE 3-continued

| | Experimental PT (hr) | Estimate PT (hr) |
|---|---|---|
| 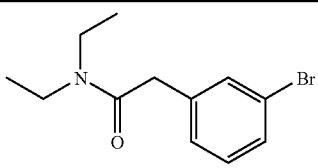<br>N,N-diethyl-2-(3-bromo-phenyl)-acetamide<br>(DM 34-1) | 0.63<br>($ED_{50}$ = 12.9) | 0.39 |
| 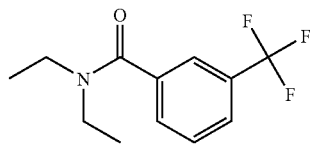<br>N,N-diethyl-3-trifluoromethyl-benzamide<br>(DM-35-3) | 0.5<br>($ED_{50}$ = 10.0) | 0.12 |
| 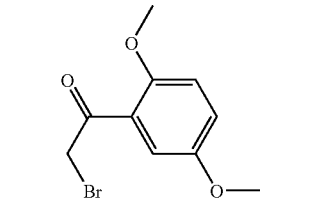<br>2-bromo-1-(2,5-dimethyloxy-phenyl)-ethanone | 2.6<br>($ED_{50}$ = 53.3) | 0.34 |
| 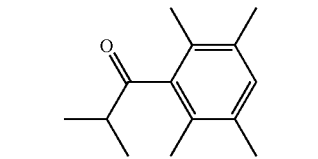<br>2-methyl-1-(2,3,5,6-tetrahmethyl-phenyl)-propan-1-one | 9.3<br>($ED_{50}$ = 188.4) | 1.2 |
| 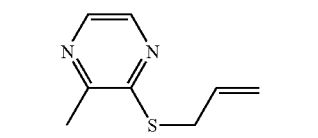<br>2-allylsufanyl-3-methyl-pyrazine | 1.6<br>($ED_{50}$ = 33.3) | 0.41 |
| 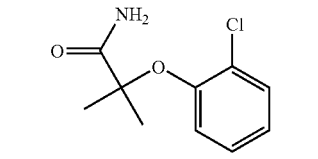<br>2-(2-chloro-phenoxy)-2-methyl-propionamide | 2.6<br>($ED_{50}$ = 53.0) | 1.4 |

FIGS. 4A to 4D show the pharmacophore model of the present invention mapped on to the compounds provided in Table 3.

Therefore, the present invention also provides a method of screening candidate compounds for repellent activity comprising using the pharmacophore of the present invention. Additionally, the present invention provides methods of using N,N-diethyl-2-(3-trifluoromethyl-phenyl)-acetamide, 2-cyclohexyl-N,N-diethylacetamide, N,N-diethyl-2-(3-bromo-phenyl)-acetamide, N,N-diethyl-3-trifluoromethyl-benzamide, 2-bromo-1-(2,5-dimethoxy-phenyl)-ethanone, 2-methyl-1-(2,3,5,6-tetramethyl-phenyl)-propan-1-one, 2-allylsufanyl-3-methyl-pyrazine, 2-(2-chloro-phenoxy)-2-methyl-propionamide, 5-[5-(1-hydroxy-nonyl)-tetrahydro-furan-2-yl]-pentanoic acid, or a combination thereof to repel arthropods.

The pharmacophore models of the present invention can be used to evaluate repellent activity and potency of a candidate compound. The candidate compounds being evaluated may be designed de novo using the models of the invention, or alternatively, be a compound, e.g., chosen from a library of compounds. Using the pharmacophore model of the invention and the methods of identification disclosed herein, one may predict the repellent potency of a candidate compound based upon its fit with the pharmacophore model of the invention. Further, one may even predict the relative degree of repellent potency via the methods of the invention by calculation of the $K_1$ (apparent) value for a compound.

After identifying a candidate compound to be evaluated for repellent potency, the three-dimensional structure of the compound may be determined. This may already have been done if, e.g., the compound was obtained from a structural database wherein three-dimensional x, y and z coordinates were used to define the compound. Alternatively, the three-dimensional structures of small molecules can be readily determined by methods known to those of skill in the art, including but not limited to, X-ray crystallography, nuclear magnetic resonance spectrometry, etc. The structures obtained from structural databases are usually the structures of compounds alone, uncomplexed with other molecules. If the three-dimensional structure is not known, one may use computer programs, such as CATALYST®, to predict the three-dimensional structure of the compound. Three-dimensional conformers may be generated from a starting structure using methods well known in the art such as the Best or Fast Conformational Analyses (Molecular Simulations, Inc., San Diego, Calif.) with an energy set to a range of 0 to 50 Kcal/mol, preferably 0 to 35 Kcal/mole, and most preferably 0 to 10 Kcal/mole, and the maximum number of conformations set to 100, preferably 175, and most preferably 255. The pharmacophore model may be then compared to a given compound using tools to compare the structural features of each, such as COMPARE™ within the VIEW HYPOTHESIS™ workbench (Molecular Simulations, Inc., San Diego, Calif.).

The degree of fit of a particular compound structure to the pharmacophore model may be calculated by determining, using computer methods, if the compound possesses the chemical features of the model and if the features can adopt the necessary three-dimensional arrangement to fit the model. The modeling program will indicate those features in the model having a fit with the particular compound.

In preferred embodiments, the present invention encompasses compounds that exhibit repellent activity and map well to the pharmacophore model disclosed herein. For example, methods for suitably superimposing compounds on a three-dimensional representation of the pharmacophore model of the present invention using computational methods is well known to those of skill in the art. A superposition of structures and the pharmacophore model is defined as a minimization of the root mean square distances between the centroids of the corresponding features of the molecule and the pharmacophore. A Van der Waals surface is then calculated around the superimposed structures using a computer program such as CERIUS™ (Molecular Simulations, Inc., San Diego, Calif.).

The compounds of the present invention may be made according to methods known in the art.

Since the pharmacophore of the present invention was created using a training set of repellent compounds, the present invention also provides methods of using the pharmacophore to screen for at least one compound that exhibits repellent activity against pests such as arthropods including mosquitoes, sand flies, ticks, chiggers (mites), and the like.

Arthropods are members of the phylum Arthropoda and have segmented bodies with paired, segmented appendages, bilateral symmetry, a dorsal heart, a ventral nerve cord, and an exoskeleton. The arthropods are divided into five classes: Insecta (insects), Arachnida (mites, ticks, spiders and scorpions), Crustacea (crabs, lobsters, shrimps, water fleas), Chilopoda (centipedes), and Diplopoda (millipedes).

Arthropods include mosquitoes, sand flies, ticks, chiggers (mites), fleas, bed bugs, black flies, tsetse flies, deer flies, horse flies, eye gnats, assassin and kissing bugs, and the like.

In accordance with a convention used in the art, ⌢ and "—" as, for example, in "—R" are used in structural formulas herein to depict the bond that is the point of attachment of the moiety or substituent to the core or backbone structure.

Where chiral carbons are included in chemical structures, unless a particular orientation is depicted, both stereoisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable substituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3-14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

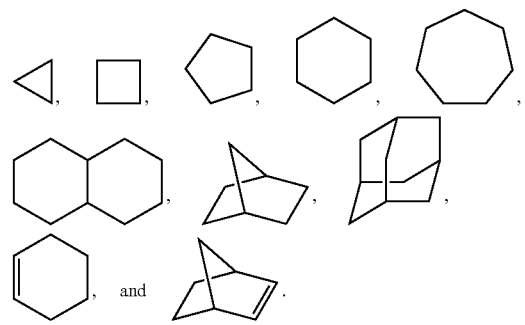

A "heterocycloalkyl" is intended to mean a non-aromatic monovalent monocyclic, bicyclic, or tricyclic radical, which is saturated or unsaturated, comprising 3-18 ring members, which includes 1-5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

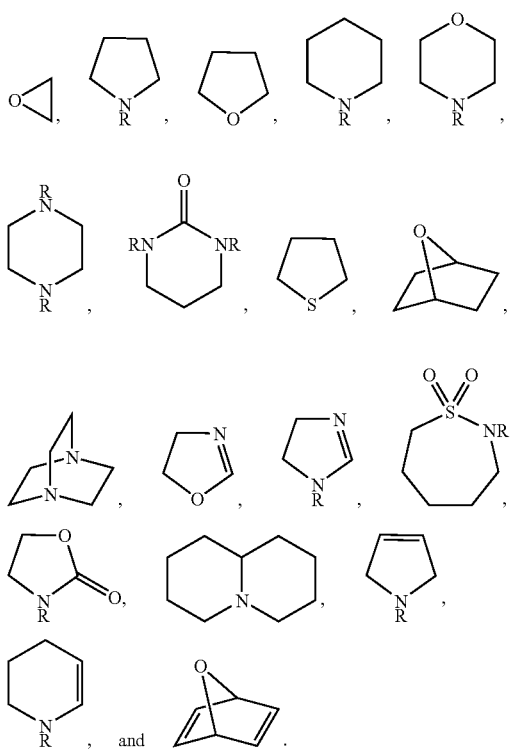

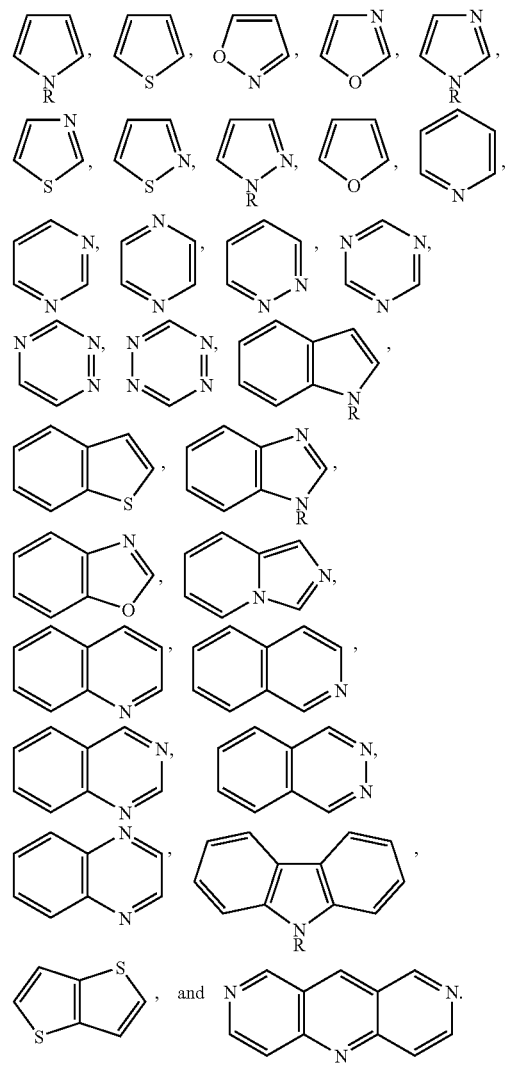

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

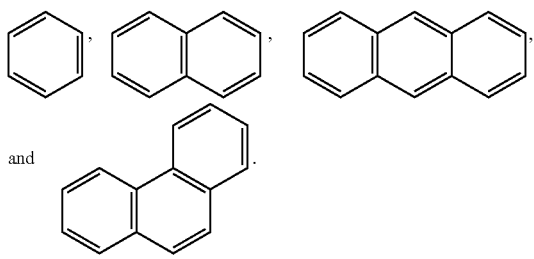

A "heteroaryl" is intended to mean an aromatic monovalent monocyclic, bicyclic, or tricyclic radical comprising 4-18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —$SO_2 R^a$ radical, where $R^a$ is a suitable substituent as defined below.

A "hydroxyl" is intended to mean the radical —OH.

An "amino" is intended to mean the radical —$NH_2$.

An "alkylamino" is intended to mean the radical —$NHR^a$, where $R^a$ is an alkyl group.

A "dialkylamino" is intended to mean the radical —NR$^a$R$^b$, where R$^a$ and R$^b$ are each independently an alkyl group.

An "alkoxyl" is intended to mean the radical —OR$^a$, where R$^a$ is an alkyl group. Exemplary alkoxyl groups include methoxyl, ethoxyl, propoxyl, and the like.

An "alkoxycarbonyl" is intended to mean the radical —C(O)OR$^a$, where R$^a$ is an alkyl group.

An "alkylsulfonyl" is intended to mean the radical —SO$_2$R$^a$, where R$^a$ is an alkyl group.

An "alkylaminocarbonyl" is intended to mean the radical —C(O)NHR$^a$, where R$^a$ is an alkyl group.

A "dialkylaminocarbonyl" is intended to mean the radical —C(O)NR$^a$R$^b$, where R$^a$ and R$^b$ are each independently an alkyl group.

A "mercapto" is intended to mean the radical —SH.

An "alkylthio" is intended to mean the radical —SR$^a$, where R$^a$ is an alkyl group.

A "carboxyl" is intended to mean the radical —C(O)OH.

A "carbamoyl group" is intended to mean the radical —C(O)NH$_2$.

An "aryloxyl" is intended to mean the radical —OR$^c$, where R$^c$ is an aryl group.

A "heteroaryloxyl" is intended to mean the radical —OR$^d$, where R$^d$ is a heteroaryl group.

An "arylthio" is intended to mean the radical —SR$^c$, where R$^c$ is an aryl group.

A "heteroarylthio" is intended to mean the radical —SR$^d$, where R$^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3$^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamide; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See e.g. Lee, et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See e.g., Bertolini, G, et al., (1997) J. Med. Chem. 40:2011-2016; Shan, D, et al., *J. Pharm. Sci.,* 86(7):765-767; Bagshawe K (1995) Drug Dev. Res. 34:220-230; Bodor, N (1984) Advances in Drug Res. 13:224-331; Bundgaard, H *Design of prodrugs* (Elsevier Press, 1985); and Larsen, I. K., *Design and Application of Prodrugs,* Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful for repelling pests such as arthropods. The compounds of the present invention may be integrated in or on objects such as clothing, paint coatings in the wall, wall-paper coatings, bed nets, curtains, window screens, ground cloths, tents, protective overgarments, and the like. See e.g. Gilbert, I H and Gouck, H K (1953) Florida Entomologist 36:47-51; Gupta, R K, et al. (1989) J. Am. Mosq. Control Assoc. 5:176-179; Armed Forces Pest Management Board. *Personal Protective Measures Against Insects and Other Arthropods of Military Significance*. Washington, D.C.: AFPMB: 2001. Technical Information Memorandum 36; Curtis, C F, et al. (1996) Med. Vet. Entomol. 10:1-11; Lindsay, I S and McAndless, J M (1978) Mosq. News. 38:350-356, which are herein incorporated by reference.

The compounds and formulations of the present invention may also be used as area repellents, also referred to as space repellents, which generally applied to a limited area and are designed to reduce or eliminate arthropod biting in the treated area. Space repellents fill the void between personal topical repellents and large-scale area insecticidal control of arthropod vectors.

The compounds and formulations of the present invention may also include lotions, creams, foams, soaps, aerosols, sticks, and towelettes, face paints (e.g. camouflage), and the like for topical application. Montemarano and colleagues have shown that sequential use of sunscreen and insect repellent results in reducing the sun protection factor (SPF) by 28%. See Montemarano, A D, et al. (1997) *Lancet*. 349:1670-1671. Example 5, provides a method for evaluating the repellent activity of the compounds of the present invention when formulated with an ingredient that may affect the repellent activity of the compound, such as sunscreen, or used in conjunction with the ingredient.

The specification for the dosage unit forms of the invention are dictated by and directly dependent on the unique characteristics of the active compound and the particular pest to be repelled, and the limitations inherent in the art of compounding such an active compound for the treatment of individuals. In general, formulations containing greater concentrations of active ingredient provide more effective and long-lasting protection. Aesthetic acceptance of the repellent by the user, though, has a major impact on the amount used and the frequency of use of the various products.

A compound of the present invention may be administered in an effective amount to a mammal such as a human or to an object. An "effective amount" is intended to mean that amount of a given repellent compound that is sufficient to repel a pest such as an arthropod as compared to a control. The amount of a given compound of the present invention that will correspond to such an amount will vary depending upon factors such as the given compound, the pharmaceutical or cosmetic formulation and route of administration, the type of pest to be repelled, and the like, but can nevertheless be routinely determined by one skilled in the art. An "effective amount" of a compound of the present invention may be readily determined by one of ordinary skill by routine methods known in the art.

For example, an effective amount of a compound of the invention ranges from about 0.1 to about 1,000 $\mu g/cm^2$ of surface area, preferably about 1 $\mu g/cm^2$ to about 500 $mg/cm^2$, preferably about 1 $\mu g/cm^2$ to about 250 $mg/cm^2$, preferably about 1 $\mu g/cm^2$ to about 100 $mg/cm^2$, preferably about 1 $\mu g/cm^2$ to about 50 $mg/cm^2$, preferably about 1 $\mu g/cm^2$ to about 25 $mg/cm^2$, more preferably about 1 $\mu g/cm^2$ to about 10 $mg/cm^2$, most preferably about 1 $\mu g/cm^2$ to about 5 $mg/cm^2$. In some embodiments, the observed $ED_{50}$ value of arthropod repellent activity ranges about 3.0 $\mu g/cm^2$ to about 21 $\mu g/cm^2$.

Preferred topical formulations include about 0.1% to about 10% of at least one compound of the present invention in a formulated salve. The skilled artisan will appreciate that certain factors may influence the concentration or amount required to effectively repel a pest, including but not limited to the type of pest, environmental conditions, geographical areas, and the like.

Methods for repelling a pest according to the present invention may consist of a single administration of a least one compound of the present invention, or alternatively comprise a series of applications. For example, a subject or object may be treated with a compound of the present invention at least once. However, the subject or object may treated with the compound from about one time per week to about once daily or multiple times daily for a given treatment period. The length of the treatment period will depend on a variety of factors such as the type of pest to be repelled, environmental conditions, risk of exposure to the given pest to be repelled, the concentration and activity of the compounds of the present invention, or a combination thereof.

The pharmaceutical and cosmetic formulations of the invention comprise at least one compound of the present invention and may be prepared in a unit-dosage form appropriate for the desired mode of administration. The pharmaceutical formulations of the present invention may be administered by any suitable route including oral, rectal, nasal, topical (including buccal and sublingual), vaginal and parenteral (including subcutaneous, intramuscular, intravenous and intradermal). In preferred embodiments, the compounds of the present invention are topically administered to a subject or placed on or integrated into an object from which a given pest is to be repelled.

The formulations of the present invention comprise an effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with given pests to be repelled.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflomithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary compounds also include other repellent compounds known in the art such as N,N-diethyl-m-toluamide (DEET), dimethyl phthalate, dibutyl phthalate, and ethyl hexanediol, Indalone, permethrins, diisopropyl adipate, benzophenone, citronella, turpentine, N,N-diethylphenylacetamide (DEPA), and the like.

Supplementary compounds also include insecticides and pesticides known in the art such as permethrins, pyrethorids, rotenone, nicotine, azadirachtin, dichlorodiphenyltrichloroethane (DDT), methoxychlor, dieldrin, dicofol, endosulfan, parathion, malathion, diazion, phosmet, chlorpyrifos, carbaryl, aldicarb, methomyl, diflubenzuron, tebufenozide, methoxyfenozide, juvenile hormone, methoprene, pyriproxyfen, diofenolan, precocenes, and the like.

The formulations of the invention may be manufactured in manners generally known for preparing pharmaceutical and cosmetic compositions, e.g., using conventional techniques such as mixing, dissolving, granulating, dragee-making, levigating, emulsifying, encapsulating, entrapping or lyophilizing. The formulations may be formulated in a conventional manner using one or more physiologically acceptable carriers, which may be selected from excipients and auxiliaries that facilitate processing of the active compounds into preparations which can be used pharmaceutically or cosmetically.

For topical formulations of the present invention, pharmaceutically acceptable excipients or cosmetically acceptable carriers and additives include solvents, emollients, humectants, preservatives, emulsifiers, pH agents, and the like. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, face paints, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art. The compounds of the present invention may be in powder form for constitution with a suitable vehicle, e.g., sterile pyrogen-free water, before use. The formulations of the present invention may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

It has been found that the repellent activity of some compounds applied on the skin decays exponentially with time, and evaporation and absorption rates account for a substantial fraction of the loss. In addition, it is believed that abrasion (loss of topical repellent due to mechanical action such as rubbing) plays a significant role in repellent loss from skin. It has been shown that the clothing abrasions of repellent-treated skin affected the efficacy of the extended-duration formulation of DEET. See Rueda, L M, et al. (1998) J. Am. Mosq. Cont. 14:178-182, which is herein incorporated by reference. Therefore, in preferred embodiments, the compounds of the present invention are formulated into extended-duration formulations similar to those known in the art. See e.g. Gupta, R K and Rutledge, L C (1989) J. Am. Mosq. Control Assoc. 5:52-55; Gupta, R K and Rutledge, L C (1991) J. Am. Mosq. Cont. Assoc. 7:490-493; Gupta, R K, et al. (1987) J. Am. Mosq. Control Assoc. 3:556-560; and Sholdt, L L, et al. (1988) J. Am. Mosq. Control Assoc. 4:233-236, which are herein incorporated by reference.

In some embodiments, a compound of the present invention is prepared with a carrier that will prolong the repellent activity of the compound such as a controlled release formulation, prevent or inhibit degradation or loss of repellent activity, or prevent or inhibit loss of the compound due to factors such as wearing or washing off of a surface where applied. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

The formulations of the present invention may be packaged as single use applications, e.g. individual squeeze packets each having one application, or as multi-use applications, e.g. a bottle comprising more than one application.

Toxicity and therapeutic efficacy of such compounds can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosage for human use according to methods known in the art.

The following Examples are intended to illustrate, but not to limit the present invention.

Example 1

Repellent Activity Assays

The following assays may be used to assay compounds according to the present invention for repellent activity. As provided herein, test arthropod colonies such as the 16 being reared at WRAIR, AFRIMS, NAMRU-3 and NAMRU-2 which include nine mosquitoes (*Aedes aegypti, Aedes albipictus, Aedes taeniorhynchus, Anopheles albimanus, Anopheles stephensi, Anopheles dirus, Anopheles farauti, Anopheles barbirostris, Culex pipiens*), three sand flies (*Phlebotamous papatasi, P. bergeroti* or *P. kazeruni*), two ticks (*Hyloma* spp. and *Argus* spp.), and flea and chigger species may be used.

All of the above arthropod colonies are reared and maintained or a new colony will be initiated in numbers to satisfy the demand for testing and evaluation. During this study an attempt will be made to set up a flea and a chigger colony so as to be able to test the spectrum of activity of new repellents or repellent formulations as scheduled to achieve the goals of the repellent development program. During one or more stages of their life cycle, these arthropods require a blood meal either to molt to the next instar or to lay eggs. The ICR mice will be used for rearing mosquitoes, sand flies, fleas and soft ticks. Prior to use, the ICR mice are sedated with 1 mg/kg of body weight with Ketamine, 1 mg/kg of body weight with Rompum. The sedatives will be diluted in 0.9% saline solution at a ratio of 1:5:16. After feeding, the ICR mice will be euthanized with carbon dioxide asphyxiation followed by cervical dislocation and carcasses will be frozen.

Guinea pigs will be utilized in maintaining colonies of hard ticks. Prior to use, the guinea pigs are sedated with 2.4 mg/kg of ketamine to reduce the easily excitable behavior of the guinea pig. A known number of ticks are allowed to feed on the guinea pigs and all ticks are recovered after the feeding. Guinea pigs are used for two to three feedings per month or as needed based upon the success of previous feeding. The guinea pigs will be euthanized with carbon dioxide asphyxiation followed by pneumothoracotomy and carcasses will be frozen. The guinea pigs will be replaced each month because they develop an immune response to the attachment of ticks which prevents their further use.

A. In Vitro Blood-Feeding System

This test system comprises a mosquito blood feeder, having a constant temperature water circulator to warm the blood, and the test cage. The blood feeder has five circular blood reservoirs, each of which is filled with outdated human blood obtained from Walter Reed Army Medical Center and certified safe according to Blood Bank testing procedures. WRAIR Policy Letter 95-20, "Bloodborne Pathogen Exposure" safety procedures will be followed for handling of human blood. The blood is replenished with adenosine triphosphate (ATP), without which the mosquitoes will not feed freely. See Rutledge, et al. (1964) Mosq. News 24:407-419, which is herein incorporated by reference. The blood is maintained at 37° C. with water from the constant temperature water circulator. The blood-filled reservoirs are covered with Baudruche membrane. The technical grade test materials in various concentrations are applied on this membrane at random, including the control. The mosquitoes to be tested are given access to the blood reservoirs on a "free choice" basis by means of a sliding door in the bottom of the test cage. Only the minimum necessary replications are done to ensure reproducibility of the test results.

Specifically, a Bauderuche membrane (inner lining of bovine large intestine) available from Joseph Long Inc. (Belleview, N.J.) is cut to cover the surface of the wells. For the standard 5-well blood-feeder, 4.5 cm squares are cut. ATP (disodium salt, mol. wt. 551.2) is weighed out. For each 26 ml of human blood, 72 mg of ATP is weighed out. The opened ATP is kept in the refrigerator. (Store at −70° C. for long term). On the day of a test, 26 ml of blood is mixed with the 72 mg of ATP to form a blood solution. The mosquitoes used should be between 5 and 15 days old. The age can be calculated from the date on the cage.

About 250 female mosquitoes are transferred from holding cartons to the clear plastic testing cage. On a testing day, the mosquitoes should be transferred to the testing cage in the morning if the test is to be performed in the afternoon. This acquaints the mosquitoes with their new environment, so they are more comfortable and feed easier.

Desired dilutions of the test repellent to be used may be prepared according to methods known in the art.

The hoses on the circulator are attached to the feeder. A film of vacuum grease is placed on the edges of the wells to hold the membranes in place. 26 ml of blood is mixed with 72 mg of ATP. The blood mixture is poured into the wells of the feeder. The membranes are placed over the wells. The circulator is turned on and the water in the circulator and the blood are allowed to warm up to about 37° C.

The repellent test dilutions are applied to the membranes with a 25 µl Eppendorf pipette and spread with a small, clean glass rod. 25 µl of the stock diluent is applied to the control a similar manner.

The membranes are allowed to dry for about 5 minutes after which the test cage is set on the membrane feeder and the trap door is opened for 20 minutes. The number of mosquitoes probing and feeding on each well is recorded at two minute intervals.

B. In Vitro Filter Paper System

The in vitro filter paper test is used for evaluation of the repelling activity of test compounds against chiggers and ticks. Four filter papers are treated with serial dilutions of a test repellent in ethanol and one with ethanol alone as a control. The filter papers are then allowed to dry for 5 minutes and then placed in glass crystallizing dishes for testing. A beveled aluminum or metal disk is then placed on the center of the each filter paper and arthropods are placed on the center of the disk. The number of arthropods moving on the disk (repellent success), moving on the filter paper (repellent failure) and immobile on the filter paper (success by morbidity) are recorded every 10 minutes for 30 minutes, and the total for each is converted to percentages of the control total for analysis.

C. ICR Mouse Assay

The ICR mouse assay used for evaluation of the repellent activity of test compounds against mosquitoes, fleas and ticks. In this test system, the whole bodies of ICR mice (7-10 days old) are treated with the test repellent by wetting them by pipette to the point of runoff. The control and treated ICR mice are placed randomly into separate compartments of a test jar or cage containing the arthropods. The arthropods can disperse throughout the test cage and feed on any of the mice. Data from previous studies have indicated that a typical mosquito feeding time is about 90 to about 120 seconds. Therefore, the feeding counts are made at 2-minute intervals for 20 minutes and the total number of bites that each mouse received is recorded. After the test, the ICR mice are euthanized with carbon dioxide asphyxiation followed by cervical dislocation and carcasses are frozen for disposal. Enough replicates are conducted to obtain a valid estimate of the $EC_{50}$ (concentration needed to repel 50% of the test population) of the test repellent.

For mosquitoes, 100 adult females are placed into a 25×25×25 cm wire-screen/plastic test cage. The test mosquitoes should be about 5 to about 15-day old nulliparous.

For fleas, 75 adult fleas are placed into a 20 cm diameter glass test jar. About ½ inch of ground corncob is placed in the jar as a substrate for the fleas.

For soft and hard backed ticks, 50 larvae, nymphs or adults (depending on the tick life stage to be tested) of ticks are placed into 20 cm diameter glass test jar. About ½ inch of ground corncob is placed in the jar as a substrate for the ticks. The rim of the jar is coated with petroleum jelly to prevent the ticks from crawling out.

Desired dilutions of the test compounds are made and then applied to the mice. Treated mice are incubated at 80° F. for 5 minutes (for $ED_{50}$ test) or 4 hours (for 4-hour $ED_{50}$ test). The mice are then transferred to the test cage/jar.

For mosquitoes and fleas, the number of arthropods feeding on each mouse is recorded at 2 minute intervals for 20 minutes (tallies 1 to 10).

For hard backed ticks, the numbers of ticks present on each mouse at the end of 4 hours (one tally only) is recorded.

For soft backed ticks, the numbers of ticks present on each mouse at the end of 20 minutes is recorded.

The test animals are euthanized with $CO_2$ asphyxiation followed by cervical dislocation and freeze carcasses.

D. New Zealand White Rabbit Assay

The New Zealand white rabbit assay system is used to evaluate the repellent activity of test compounds and formulations that can be diluted with ethanol, acetone, or similar inert carriers against laboratory reared mosquitoes, sand flies, and reduviid bugs. A rabbit, sedated with 15 mg/kg of ketamine injected intramuscularly into the thigh, will be placed in a plastic restrainer and its abdomen shaved with electric animal clippers. Five 29 mm diameter circles are then outlined on the shaven area with a plastic template and felt tipped pen. Dilutions of the test repellents and control diluent (ethyl alcohol) are applied at random to each circle in a constant volume at the desired dosage ($mg/cm^2$) and spread evenly over the test area. The test cage containing the arthropods is placed over the treated areas and secured with pressure sensitive adhesive tape. A plastic slide is then withdrawn and the number of bites is recorded. At the conclusion of each test, the test areas are washed and rinsed with soap and water. The test animal is monitored until recovery and then returned to the animal holding facility until used again.

The test cage is loaded with 10 female mosquitoes, 10 female sand flies, or 25 adult reduviid bugs from a given population to be tested. The rabbit is injected with Ketamine (15 mg/kg of body weight) into the thigh with a 23 gauge one and one half inch needle. 0.025 ml of the control diluent is applied evenly over a test area. 0.025 ml of each dilution of test compound is applied to a test area in a similar manner.

After 2 minutes (zero-hour $ED_{50}$ test) or after 4 hours (4 hour $ED_{50}$ test), the test areas are exposed to the arthropods. Suitable ranges of doses are determined by methods known in the art and, if desired, the assay may be replicated as necessary to determine 95% confidence limits for the $ED_{50}$ of a given test repellent.

Example 2

3D-QSAR & Pharmacophore Generation

The molecular modeling software, CATALYST®4.7 software (Accelrys Inc., San Diego, Calif.) was used to construct a three-dimensional QSAR pharmacophore model for the repellent activities exhibited by known repellent compounds. A training set of 11 compounds provided in Table 1 having a broad range of repellent activities was used to construct the pharmacophore model.

The pharmacophore model was developed by placing suitable constraints on the number of available features such as, aromatic hydrophobic or aliphatic hydrophobic interactions, hydrogen bond donors, hydrogen bond acceptors, hydrogen bond acceptors (lipid), and ring aromatic sites to describe the repellent activity of the repellent compounds.

During this pharmacophore or hypothesis generation, the molecules were mapped to the features with their pre-determined conformations generated earlier using the "fast fit" techniques in the CATALYST®. The procedure resulted in the generation of 10 alternative hypotheses for repellent activity of the compounds and appeared to perform quite well for the training set. The correlation coefficients were found to be between about 0.92 to about 0.80 for 6 of the 10 models, and the RMS values ranged between about 0.4 and about 0.6. The total costs of the hypotheses varied over a narrow range between about 41.5 to about 53.5 bits. The difference between the fixed cost and the null cost is about 62.0. Thus, both of the differences, the total cost of the first and the tenth hypothesis, and the fixed cost and the null cost were found to be within the acceptable range recommended in the cost analysis of the CATALYST® procedure.

Example 3

Cross Validation of Pharmacophore Model

The pharmacophore model may be cross-validated by generating a test set of different repellent compounds known in the art. The test set compounds may be screened for repellent activity in a manner identical to the compounds of the original training set according to Example 1 or methods known in the art. The compounds of the test set for cross validation should not be ones of the original training set used for automatic generation of the pharmacophore.

Regression analysis is performed by mapping this test set onto the features of the pharmacophore and should show remarkable consistency of the model (R greater than about 0.85, preferably greater than about 0.90, more preferably greater than about 0.95). Regression information is used to estimate activity of the training set of the compounds as well as to estimate the unknown compounds. The greater the fit of the pharmacophore with the compound, the more likely the compound will exhibit repellent activity. The regression for both the training set and the test set is calculated by the following equation:

$$-\log(\text{activity})_{Est} = \text{Fit} * \text{Slope} + Y \text{ intercept}$$

See Catalyst® Tutorials, Release 4.5, August 1999, Accelrys Scientific Support. 9685 Scranton Road, San Diego, Calif. 92121-3752, which is herein incorporated by reference.

Example 4

Pharmacophore Compound Screening

A. Database Pharmacophore Compound Screening

Three-dimensional multiconformer databases, including an in-house Chemical Information System (Chemical Information System, Division of Experimental Therapeutics, Walter Reed Army Institute of Research, Silver Spring, Md.), National Cancer Institute, IBS and Maybridge databases, were screened for potential new repellent agents using the pharmacophore model of the present invention. The Chemical Information System database of the Division of Experimental Therapeutics, WRAIR is a database of more than 245,000 proprietary compounds. By using the catDB utility program of the CATALYST®, the database was transformed into a multi-conformer based 3D database. The database searching protocol in the CATALYST® involves a rapid 3D screening process followed by a rigorous atom-by-atom mapping in which a fairly comprehensive set of features including the chemical features of the pharmacophore are considered. In addition to the traditional pharmacophore based searching, 3D shape similarity and partial match searching may also be performed. See Kurogi, Y and Gunner, O F (2001) Current Medicinal Chemistry 8:1035-1055, which is herein incorporated by reference.

A short list of 138 compounds, mostly antimalarial agents of diverse chemical structures from in-house CIS (Archives of the Chemical Information System, Division of Experimental Therapeutics, Walter Reed Army Institute of Research, 503 Robert Grant Avenue, Silver Spring, Md. 20910-7500, U.S.A.) were screened for repellent activity and the following 4 compounds were found to exhibit repellent activity against arthropods: 2-bromo-1-(2,5-dimethoxy-phenyl)-ethanone, 2-methyl-1-(2,3,5,6-tetramethyl-phenyl)-propan-1-one, 2-allylsufanyl-3-methyl-pyrazine, and 2-(2-chloro-phenoxy)-2-methyl-propionamide.

Example 5

Repellent and Sunscreen Activity Assay

Candidate combination sunscreen and arthropod repellent formulations, including camouflage face paints, may be tested for their effectiveness against arthropods as follows. The arthropods to be used may be those known in the art, those provided in Example 1, or yellow fever mosquito (*Aedes aegypti*) and the malaria vector (*Anopheles stephensi*). The arthropods should be raised and cultured according to standard methods known in the art. For example, mosquitoes will be reared and maintained at 27° C. and 80% relative humidity and a 12:12 light:dark photoperiod. Larvae will be fed a diet of liver powder, brewer's yeast and hog chow and adults will be maintained on 10% sucrose solution. The mosquitoes used for experimentation will be nulliparous females between 5 and 15 days of age.

The light source used for SPF testing is a Xenon Arc Solar simulator (150 W) (Solar Light Company, Philadelphia, Pa.). This instrument is described in detail in J. Invest. Dermatol. 53:192 (1969), which is herein incorporated by reference. The lamp output is measured with a UV intensity meter (Model 2A, Solar Light Company, Philadelphia, Pa.) before and after a test period.

The repellency portion of this study will be conducted according to the current type protocol "Testing Non-Standard Insect Repellents and Repellent Formulations in Volunteers". This protocol was approved by the Surgeon General's Human Subjects Research Review Board in October 1981. The test method was subsequently adopted by the American Society for Testing and Materials (ASTM) in 1989.

Generally, a formulation comprising an equal amount of sunscreen and arthropod repellent will be applied to the flexor region of the forearms of human volunteers. The repellent formulations will be applied at random to the flexor region of the forearms of four volunteers. There are 8 groups to be tested including 2 control groups. At the start of the test, a 4×5×18 cm plastic cage containing 15 mosquitoes will be bound to forearm with Velcro® tape, and a slide will be withdrawn to expose the repellent treated skin. The number of mosquitoes biting in the test cage will be recorded at the end of 90 seconds. New mosquitoes will be used in each test and the cages will be removed after 90 seconds. This test procedure will be repeated every two hours for 10 hours. Thus, six tests of each species of mosquitoes will be conducted on each formulation after application on the skin. The above procedure will be repeated four times. The temperature and relative humidity in the test room will be recorded on the test days. The 5% end will be employed in each test. Since there will be 15 mosquitoes per cage and 6 test periods (0, 2, 4, 6, 8, and 10 hours), this means that a test can be terminated whenever 5% of the 15×6 mosquitoes have bitten. Thus a test may be discontinued after 5 bites have been received on the repellent treated area on the forearm.

Percent repellency will be determined from the total number of bites on the control and repellent treated volunteers by converting to percentages of the total for the control and subtracting from 100.

$$\% \text{ Repellency} = 100 - \left(\frac{\text{\# of bites on treatment}}{\text{\# of bites on control}} \times 100\right)$$

Sun protection factors (SPF) of the combination sunscreen and arthropod repellent formulations will be determined in accordance with the Federal monograph of proposed rules for sunscreen testing published in the Federal Register, Vol. 43, No. 166, 25 Aug. 1978, which is herein incorporated by reference. The standard against which new sunscreen formulations are measured is an 8% Homosalate formulation (SPF 4).

Minimal erythemal dose (MED) is defined as the time interval or dosage of UVR sufficient to produce a minimal, perceptible erythema on untreated skin. Prior to the testing phase, the MED of each subject is determined by a progressive sequence of timed UVR exposures, each of which is graduated incrementally by 25% over that of the previous site. Twenty-four hours after irradiation, the sites are evaluated from erythema according to the following scoring system.

| | |
|---|---|
| 0 | Negative, no visible reaction |
| +/− | Minimal, perceptible erythema |
| 1+ | Defined erythema |

| | |
|---|---|
| 2+ | Moderate erythema |
| 3+ | Severe erythema |

A sufficient number of 5×10 cm test site areas are outlined with a surgical marking pen on the subject's back between the scapulae and the beltline, lateral to the midline. These areas are designated for the test material(s) or standard, with an adjacent site designated for a concurrent MED determination (unprotected control). A 0.1 ml or 0.1 g portion of test material(s) or standard is applied to the appropriate 5×10 cm test site and spread evenly over the site using a fingercot. This delivers a film of 2 mg/cm$^2$.

At least 15 minutes after the product application, the test site is divided into subsites which are used for a defined serial UVR exposure.

Exposure times are selected for each subsite in treated areas based upon the previously determined MED of the untreated skin and the anticipated SPF of the test material(s) or standard.

Sun protection factor is defined as the ratio of the amount of energy required to produce an MED on protected skin (treated with test material(s) or standard) to the amount of energy needed to produce an MED on untreated skin and is calculated as follows:

$$SPF = \frac{\text{Minimal Erythema Dose in sun-protected skin}}{\text{Minimal Erythema Dose in non-sunscreen-protected skin}}$$

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of repelling an arthropod from a surface of a substrate, an area, or a mammal which comprises administering to, placing or immobilizing on or in, integrating on or in the surface, the area, or the mammal an effective amount of at least one compound selected from the group consisting of 2-bromo-1-(2,5-dimethoxy-phenyl)-ethanone, 2-methyl-1-(2,3,5,6-tetramethyl-phenyl)-propan-1-one, and 2-(2-chlorophenoxy)-2-methyl-propionamide.

2. The method of claim 1, wherein the substrate is a fabric, an article of clothing, a bed net, a curtain, a paper, a wall paper, a window screen, a ground cloth, a tent, a towelette, or a protective overgarment.

3. The method of claim 1, wherein the compound is formulated into a lotion, a cream, a foam, an aerosol, a face paint, or a stick.

4. The method of claim 1, wherein the compound is integrated into a soap, a sunscreen product, or a cosmetic.

5. The method of claim 1, wherein the compound is formulated with a pharmaceutically or cosmetically acceptable carrier.

* * * * *